United States Patent
Su et al.

(10) Patent No.: US 6,391,592 B1
(45) Date of Patent: May 21, 2002

(54) BLOCKER-AIDED TARGET AMPLIFICATION OF NUCLEIC ACIDS

(75) Inventors: Xing Su, Cupertino; Weiwei Liu, Palo Alto, both of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/738,035

(22) Filed: Dec. 14, 2000

(51) Int. Cl.7 .............................. C12P 19/34; C12Q 1/68
(52) U.S. Cl. ......................... 435/91.1; 435/6; 435/91.2
(58) Field of Search ........................... 435/6, 91.1, 91.2

(56) References Cited

U.S. PATENT DOCUMENTS 4,683,195 A * 7/1987 Mullis et al. .................. 435/6
5,858,656 A * 1/1999 Deugau et al. ................ 435/6

FOREIGN PATENT DOCUMENTS

GB         2293238 A   *  3/1996
WO         WO-99/61661   * 12/1999

* cited by examiner

Primary Examiner—Kenneth R. Horlick
Assistant Examiner—Teresa E Strzelecka
(74) Attorney, Agent, or Firm—Philip McGarrigle

(57) ABSTRACT

The present invention describes a method for blocking an unwanted sequence from been amplified, duplicated or reverse transcribed by using a blocking molecule. Preferred embodiments of the blocking molecule have sequences complimentary at least partially to the unwanted sequence. The preferred blocking molecule can be made of nucleic acids and analogues, for example, peptide nucleic acid and locked nucleic acid.

28 Claims, No Drawings

BLOCKER-AIDED TARGET AMPLIFICATION OF NUCLEIC ACIDS

TECHNICAL FIELD

The present invention is in the field of genetic analysis for medical diagnosis, genetic variation research, or genetic engineering. More specifically, the present invention is in the field of nucleic acid amplification.

BACKGROUND

Many differences in living organisms, including biological traits, characteristics or disease susceptibilities, are closely related to their genetic variations. Therefore, it is desirable to understand genetic variations of organisms so that useful information can be obtained to help select organisms with desirable traits or characteristics or predict an organism's disease susceptibility and thus provide proper treatments.

Most often, the study of genetic variations, for example the study of genetic polymorphism, involves the analysis of nucleic acid sequences in DNA or RNA. The sequences of interest may be low in occurrence in nucleic acid samples. On the other hand, undesirable sequences may have high occurrence in samples. Some of these undesirable sequences are repetitive sequences. The high occurrence of unwanted sequences may cause serious interference when analyzing genetic variations because they can produce a significant background noise in genetic detection. The problem becomes more severe when an amplification process is employed to increase the copy numbers of the sequences of interest because the amplification process may amplify both interested sequences and unwanted sequences indiscriminately. The present invention is directed to decreasing the possibility of amplifying unwanted sequences during an amplification process so that sequences of interest can be amplified while unwanted sequences will not be amplified, thus decreasing the background noise in genetic variation analysis. The present invention is especially useful to suppress the amplification of repetitive sequences.

SUMMARY OF THE INVENTION

According to the present invention, methods are provided to block unwanted nucleic acid sequences from being amplified in a nucleic acid amplification process by adding blocking molecules that bind to the undesirable nucleic acids sequences and thus preventing the amplification of undesired sequences in the process. The methods can be used to block any undesirable sequences and are especially useful for blocking repetitive sequences.

In one embodiment of the invention, a method for blocking amplification of undesirable DNA sequences during a DNA amplification process comprises the following steps: providing DNA samples from cells or homogenized tissues; fragmenting the DNA by restriction enzymes or DNase followed by end modification and adapter ligation; blocking undesirable DNA sequences by peptide nucleic acids having complimentary sequences to the undesirable DNA sequences prior to or during amplifying the DNA samples by polymerase chain reaction (PCR) with proper reagents, enzymes and primers.

In another embodiment of the invention, a kit is constructed to carry out the blocking method. The kit comprises Cot-1 cRNA sequences as the blocking molecules, a restriction digestion enzyme, an adapter comprising a primer sequence and a cohesive end corresponding to the restriction site specified by the restriction enzyme, a ligase, and corresponding primers.

DETAILED DESCRIPTION

A. General

The present invention relies on many patents, applications and other references for details known to those of the art. Therefore, when a patent, application, or other reference is cited or repeated below, it should be understood that it is incorporated by reference in its entirety for all purposes as well as for the proposition that is recited.

As used in the specification and claims, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Such conventional techniques can be found in standard laboratory manuals such as *Genome Analysis: A Laboratory Manual Series* (Vols. I–IV), *Using Antibodies: A Laboratory Manual, Cells: A Laboratory Manual*, PCR Primer: *A Laboratory Manual, and Molecular Cloning: A Laboratory Manual* (all from Cold Spring Harbor Laboratory Press), all of which are herein incorporated in their entirety by reference for all purposes.

Additional methods and techniques applicable to array synthesis have been described in U.S. Pat. Nos. 5,143,854, 5,242,974, 5,252,743, 5,324,633, 5,384,261, 5,405,783, 5,412,087, 5,424,186, 5,445,934, 5,451,683, 5,482,867, 5,489,678, 5,491,074, 5,510,270, 5,527,681, 5,550,215, 5,571,639, 5,578,832, 5,593,839, 5,599,695, 5,624,711, 5,631,734, 5,677,195, 5,744,101, 5,744,305, 5,770,456, 5,795,716, 5,800,992, 5,831,070, 5,837,832, 5,856,101, 5,871,928,5,858,659, 5,936,324, 5,968,740, 5,974,164, 5,981,185, 5,981,956, 6,025,601, 6,033,860, 6,040,138, and 6,090,555, which are all incorporated herein by reference in their entirety for all purposes.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

B. Definitions

Some definitions are recited below, other definitions can be obtained from the U.S. patents and references cited herein.

Analogue when used in conjunction with a biomonomer or a biopolymer refers to natural and unnatural variants of the particular biomonomer or biopolymer. For example, a nucleotide analogue includes inosine and dideoxynucleotides. A nucleic acid analogue includes peptide nucleic acids and linked nucleic acids. The foregoing is not intended to be exhaustive but rather representative. More information can be found in U.S. patent application Ser. No. 80/630,427 which is hereby incorporated by reference as stated above.

An array is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. Arrays are described in more detail in the patents listed above.

Complementary or substantially complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementarity over a stretch of at least 14 to 25 nucleotides, preferably at least about 75%, more preferably at least about 90% complementarity. See e. g., M. Kanehisa Nucleic Acids Res. 12:203 (1984), incorporated herein by reference.

Fragment or Sequence refers to a portion of a larger DNA polynucleotide or DNA. A DNA molecule, for example, can be broken up, or fragmented into, a plurality of fragments or sequences.

Genetic variation refers to variation in the sequence of the same region between two or more organisms.

Hybridization refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

Nucleic acid refers to a polymeric form of nucleotides of any length, such as oligonucleotides or polynucleotides, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be customized to stabilize or destabilize hybrid formation or enhance the specificity of hybridization with a complementary nucleic acid sequence as desired. See U.S. Pat. No. 6,156,501 which is hereby incorporated by reference in its entirety for all purposes.

Oligonucleotide or polynucleotide is a nucleic acid ranging from at least 2, preferable at least 8, and more preferably at least 15, 18, 20, 25, 30, 35 nucleotides in length or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). See U.S. Pat. No. 6,156,051 which is hereby incorporated by reference in its entirety for all purposes. The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

Polymerase Chain Reaction or PCR refers to the method to amplify specific DNA sequences based on repeated cycles of denaturation of double-stranded DNA, followed by oligonucleotide primer annealing to the DNA template, and primer extension by a DNA polymerase. Methods of PCR have been described in U.S. Pat. Nos. 4,683,195, 4,6983, 202, and 4,800,159, which are all incorporated herein by reference in their entirety for all purposes. Additional information on PCR may be found in PCR *Technology: Principles and Applications for DNA Amplifcation* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); and *PCR* (eds. McPherson et al., IRL Press, Oxford). The specific reagents, conditions and time can be shown in the above references or by reviewing the package instructions on the products sold by ABI (foster City, California) or Roche Molecular Systems (Alameda, Calif.).

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A diallelic polymorphism has two forms. A triallelic polymorphism has three forms.

Primer is a single-stranded oligonucleotide capable of acting as a point of initiation for template-directed DNA synthesis under suitable conditions, e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 3 to 6 and up to 30 or 50 nucleotides. Short primer molecules generally require cooler temperatures to form sufficiently stable hybrid complexes with the template. A primer needs not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

Probe: A probe is a surface-immobilized molecule that can be recognized by a particular target. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, polypeptide, proteins, enzymes, enzyme substrates, cofactors, drugs, lectins, sugars, nucleic acids, oligosaccharides, and monoclonal antibodies.

Single Nucleotide Polymorphism or SNP occurs at a polymorphic site occupied by a single nucleotide, which is the site of variation between allelic sequences. This site of variation is usually both preceded by and followed by highly conserved sequences e.g., sequences that vary in less than $1/100$ or $1/1000$ members of the populations of the given allele. A SNP usually arises due to the substitution of one nucleotide for another at the polymorphic site. These substitutions include both transitions (i.e. the replacement of one purine by another purine or one pyrimidine by another pyrimidine) and transversions (i.e. the replacement of a purine by a pyrimidine or vice versa). SNPs can also arise from either a deletion of a nucleotide or from an insertion of a nucleotide relative to a reference allele.

Substrate refers to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

Blocker or blocking compound refers to a molecule that has 2 components, it hybridizes to its complementary sequences (targets), and the hybrids prevent the complemetary sequences (targets) from being used as templates for sequence synthesis. Complementary in this situation is not strictly interpreted as nucleic acid sequence homology, but includes those molecules that bind in a similar manner as ligands and antiligands, targets and receptors, antibodies and their antigens (which can be nucleic acids, proteins or other molecules), and any molecule that stereochemically recognizes another.

C. The Methods

One aspect of the present invention provides a novel method to prohibit undesirable nucleic acid sequences from being amplified in an amplification process, preferably in a PCR process. Consequently, the concentration of desirable nucleic acids is increased relative to the undesirable nucleic acids. One essential part of the invention is to use blocking molecules to block the undesirable sequences so that synthesis of the complimentary sequence by enzymatic means or other chemical means, which use the blocked sequences as template, can not be completed. At the same time, the sequences that do not contain the undesirable regions are not blocked and thus can be synthesized completely. In the process of amplification, the complete sequences can be used as template for the next round of synthesis while the incomplete sequences can not. The net result after a number of cycles of amplification is that synthesis of undesirable sequences is reduced and synthesis of target sequences is carried out normally. Therefore, the present invention allows selective prohibition of amplification of certain nucleic acids sequences. This invention can be used in any amplification process that requires an existing nucleic acid sequence as a template and is not limited to PCR.

Other suitable amplification methods include the ligase chain reaction (LCR) (e.g., Wu and Wallace, *Genomics* 4, 560 (1989) and Landegren et al., *Science* 241, 1077 (1988)), transcription amplification (Kwoh et al., *Proc. Natl. Acad. Sci. USA* 86, 1173 (1989)), self-sustained sequence replication (Guatelli et al., *Proc. Nat. Acad. Sci. USA*, 87, 1874 (1990)) and nucleic acid based sequence amplification (NABSA). The latter two amplification methods include isothermal reactions based on isothermal transcription, which produce both single-stranded RNA (ssRNA) and double-stranded DNA (dsDNA) as the amplification products in a ratio of about 30 or 100 to 1, respectively.

The blocking effect of the present invention is based on template-dependent duplication of nucleic acids. Therefore, the present invention is suitable for blocking nucleic acid amplification in transcription amplification, self-sustained sequence replication, and nucleic acid based sequence amplification.

The present invention may also be used to block unwanted mRNA from being transcripted in in vitro reverse transcription of mRNA. Preferably, the blocking should target the sequences near the 3' end of MRNA. More preferably, the blocking molecule may have complimentary sequences to the sequences immediately nest to the 3' poly(A) end of the unwanted MRNA molecule.

Nucleic acid amplification is frequently used in genetic analysis, especially in gene expression monitoring and genotyping. In one embodiment, the present invention is used to provide a suitable sample preparation method for the detection of SNP. One of the preferred embodiments of the detection of SNP is to hybridize nucleic acid samples to a plurality of polynucleotide probes, or arrays. Ideally, such arrays are immobilized on a solid substrate.

Substrates having a surface to which arrays of polynucleotides are attached are referred to herein as "biological chips". The substrate may be, for example, all types of silicon, fused silica or glass, and can have the thickness of a microscope slide or glass cover slip, or thinner or thicker. Substrates that are transparent to light are useful when the assay involves optical detection, as described, e.g., in U.S. Pat. No. 5,545,531, the disclosure of which is incorporated herein. Other substrates include Langmuir Blodgett film, germanium, (poly)tetrafluorethylene, polystyrene, gallium arsenide, gallium phosphide, silicon oxide, silicon nitride, and combinations thereof. More information about substrates can be found in the array patents that are incorporated by reference above.

In the embodiment wherein arrays of nucleic acids are immobilized on a surface, the number of nucleic acid sequences may be selected for different applications, and may be, for example, about 50, 100, 400, 500, 750, 1000, 2,000, 5,000, $10^5$, $10^6$, $10^7$, or $10^8$. In one embodiment, the surface comprises at least 100 probe nucleic acids each preferably having a different sequence, each probe contained in an area of less than about 0.1 cm$^2$, or, and each probe nucleic acid having a defined sequence and location on the surface. In one embodiment, at least 400, 1,000, 5,000, 10,000, 100,000 or more different nucleic acids are provided on the surface, wherein each nucleic acid is contained within an area less than about $10^{-3}$ cm$^2$, as described, for example, in U.S. Pat. No. 5,510,270. Additional information may be found in the array patents referred elsewhere in this application, which are incorporated for all purposes.

Arrays of nucleic acids for use in gene expression monitoring and genotyping are described in PCT WO 98/15151, and U.S. Pat. Nos. 6,040,138, 6,033,860, 5,871,928, 5,800, 992, 6,027,880, 6,027,894, 5,968,740, 5,925,525, 5,858,659, 5,710,000, 5,974,164, 5,856,104 and 5,795,716 each of which is hereby incorporated by reference for all purposes. In one embodiment, arrays of nucleic acid probes are immobilized on a surface, wherein the array comprises more than 100 different nucleic acids and wherein each different nucleic acid is localized in a predetermined area of the surface, and the density of the different oligonucleotides is greater than about 60 different oligonucleotides per 1 cm$^2$.

Methods for screening using arrays of polymers, such as nucleic acids, immobilized on a solid substrate, are disclosed, for example, in U.S. Pat. No. 5,510,270, the disclosure of which is incorporated herein. In this method, an array of diverse nucleic acids is formed on a substrate. The fabrication of arrays of polymers, such as nucleic acids, on a solid substrate, and methods of use of the arrays in different assays, are described in: U.S. Pat. Nos. 5,143,854, 5,242,979, 5,252,743, 5,324,663, 5,384, 261, 5,405,783, 5,412,087, 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070, 5,856,011, 5,858,695, 5,861,242, 5,871,928, 5,874,219, 5,858,837,5,919523, 5,925,525, 5,959,098, 5,968,740, 5,981,185, 6,013,440, 6,022,963, 6,027,880, 6,040,138, 6,045,996, and 6,083,697 all of which are incorporated by reference in their entirety for all purposes. The above disclosures describe various methods of fabricating nucleic acid arrays, including spotting pre-made probes onto a solid support and synthesizing probes directly onto the support. Any of the arrays and methods of manufacturing arrays disclosed in the above references are suitable for use in the presently claimed invention.

Methods for labeling nucleic acids can be found in U.S. patent application Ser. No. 08/882,649, filed Jun. 25, 1997, hereby incorporated by reference in its entirety, and in commercial products such as those sold by Enzo Biochem.

Accessing genetic information using high density DNA arrays is further described in Chee, Science 274:610–614 (1996), the disclosure of which is incorporated herein by reference.

One advantage of using high density arrays for genotyping is the ability to interrogate SNPs and polymorphisms at multiple sites or on different genes. Those skilled in the art will appreciate that it is difficult to detect multiple SNPs by amplifying nucleic acid with specific primers because the use of multiple specific primers is costly and time consuming. On the other hand, random priming or semi-random priming, or priming according to an adapter sequence is cheap and simple to amplify multiple nucleic acid sequences. However, because random priming or semi-random priming, or priming according to an adapter sequence is not specific, unwanted sequences may also be amplified. High concentration of unwanted sequences can interfere with detection of multiple SNPs. The use of the present invention will significantly decrease the interference caused by the high concentration of unwanted sequences produced during amplification of nucleic acids thus enabling the utilization of high density arrays to detect multiple gene SNPs.

Those skilled in the art will appreciate that there are many ways to obtain appropriate nucleic acid samples for the purpose of genetic research and analysis. Nucleic acid samples may be samples derived from any number of sources including genomic DNA, cDNAs, pools of fragments, cloned sequences, etc. Any suitable biological sample can be used for assay of genomic DNA. Convenient suitable tissue samples include whole blood, semen, saliva, tears, urine, fecal material, sweat, buccal, skin and hair. Pure red blood cells are not suitable. As those skilled in the art will appreciate, for assays of cDNA or mRNA, the tissue sample must be obtained from an organ in which the target nucleic acid is expressed, e.g., the liver for a target nucleic acid of a cytochrome P450.

Although nucleic acid samples can be amplified without specific treatments, as one of skill in the art will appreciate, longer DNA fragments are more difficult to amplify with high fidelity. Preferably, these samples are fragmented before amplification. Any known method of fragmentation may be employed. Various methods of fragmenting nucleic acids are known to those of skill in the art. These methods may be, for example, either chemical or physical in nature. Chemical fragmentation may include partial degradation with a DNAse, partial depurination with acid, restriction enzymes or other enzymes that cleave nucleic acid at known or unknown locations. Physical fragmentation methods may involve subjecting the nucleic acid to a high shear rate. High shear rates may be produced, for example, by moving nucleic acid through a chamber or channel with pits or spikes, or forcing the nucleic sample through a restricted size flow passage, e.g., an aperture having a cross-sectional dimension in the micron or submicron scale. Combinations of physical and chemical fragmentation methods may likewise be employed, such as fragmentation by heat and ion-mediated hydrolysis. More information regarding sample preparation can be found in U.S. patent applications Ser. Nos. 09/428,350, 60/105,867, 60/136,125, 60/162,739, 60/191,345 and 60/228,253, which are all incorporated herein by reference in their entirety for all purposes.

Those of skill in the art will be familiar with the digestion of nucleic acids with restriction enzymes. In a preferred embodiment of the invention, particularly when genomic DNA is used as the sample source, a combination of restriction enzymes is used, as specific combinations of restrictions enzymes may result in a larger percentage of genomic DNA fragments of suitable length for amplification.

A specific restriction enzyme will typically cut the DNA at a given recognition sequence, and that recognition sequence statistically appears in the genomic DNA every X number of base pairs, where X varies with the length of the given recognition sequence (i.e., restriction enzymes that have a four-base recognition site will cut more frequently than restriction enzymes with a six- or eight-base recognition site). Thus, the combination of restriction enzymes be used may be altered to produce fragments in a desired range of sizes.

A fragmentation can involve several fragmentation methods. For example, a fragmentation can start with a physical method and be followed by an enzymatic digestion. The enzymatic digestion may employ one enzyme or more than one enzymes.

It might be desirable to modify fragmented nucleic acid samples. In one embodiment of the present invention, adapters are attached to the fragments. Adapter sequences and their uses are well known to those skilled in the art. Such information can be found in Maniatis, et al., "Molecular Cloning: A Laboratory Manual," $2^{nd}$ Ed. Cold Spring Harbor Laboratory Press, Cold Spring Harbor, N.Y. (1989) ("Maniatis et al."). An adapter can be used as a complimentary sequence for a primer; as a label; to introduce a special functional sequence, such as an RNA promoter region or restriction site; or as separation elements or any desired use. Typically adapters are short oligonucleotides of known sequence between 5 and 20 bases in length, but they can be much longer as desired for a particular application.

In the embodiment in which the DNA is fragmented with known restriction enzymes, adapters may be designed to specifically hybridize to the known overhangs, or cohesive ends, produced by the specific restriction enzymes used. If these adapters will later be used as primer sites for PCR, it may be desirable to design adapters containing sequences that are known to be appropriate PCR priming sequences. Alternatively, if a linear method of amplification is to be used, such as that described in International PCT Application WO 90/06995, one or more of the adapters may also include a promoter sequence.

Alternatively, if methods of fragmentation are employed such that the ends of the fragments are unknown, the ends of the fragments may be filled in with the appropriate nucleotides, for example, by the use of T4 DNA polymerase, and adapters may be blunt-end ligated to the fragments. Methods of filling in DNA overhangs are known to those of skill in the art. See, for example, Ausubel, et al., (Eds), Current Protocols in Molecular Biology, Section 3.5.9 and throughout. Blunt end hybridization is described in, for example, Ausubel, et al., (Eds) (Sections 3.143.2 and 3.16.8). Of course this method may be employed even when the ends of the fragments are known.

One essential step of the present invention is adding blocking molecules to nucleic acid samples to prevent amplification of an undesirable sequence. A typical blocking molecule is any molecule that is capable of binding a specific region of an undesirable nucleic acid sequence, thus interrupting the synthesis of the undesirable nucleic acid sequence. Additionally, the blocking molecule must not be capable of serving as starting molecule of nucleic acid synthesis. Such blocking molecules may comprise at least proteins, nucleic acids or their analogues.

In one embodiment of the present invention, peptide nucleic acids are used as the blocking molecules. Unlike nucleic acids in which nucleotides are linked with phosphodiester bonds, nucleotides in peptide nucleic acids are linked with polyanide backbones. Given the same sequences, a peptide nucleic acid sequence has a higher affinity for the same complimentary nucleic acids sequence than a normal nucleic acid sequence has. In addition, peptide nucleic acids can not serve as a starting molecule, or a primer, for nucleic acid polymerases. In other words, they are unextendable to nucleic acid polymerases. Peptide nucleic acids that comprise a polyamide backbone and the bases found in naturally occurring nucleosides are commercially available. Those skilled in the art will know how to synthesis peptide nucleic acids. Peptide nucleic acid polymers with desired sequences are also commercially available.

Similarly, locked nucleic acids are suitable blocking molecules. Like peptide nucleic acids, locked nucleic acids have a high affinity to nucleic acids and not extendable. In addition, locked nucleic acid polymers with specific sequence are commercially available.

In another embodiment, an end-modified nucleic acid sequence is used as the blocking molecule. The purpose of end-modification is to make the sequence unextendable to nucleic acid polymerases. There are many ways to make such modifications. Preferably, if a DNA sequence is used as the blocking molecule, the sequence is modified by attaching a dideoxyribonucleotide to one end or both ends of the sequence. Specifically, such modification could be attaching a 2',3'-dideoxyribonucleotide to the 3' end of the sequence, or a 2',5'-dideoxyribonucleotide to 5' end of the sequence, or a 2',3'-dideoxyribonucleotide to the 3' end of the sequence and a 2',5'-dideoxyribonucleotide to the 5' end of the sequence. There are many ways to synthesize a DNA sequence. Services to synthesize a specific DNA sequence are readily available. DNA sequences can be synthesized from a DNA synthesizer (ABI, Foster City, Calif.). Specific DNA sequences may also be obtained by PCR. A person skilled in the art will know that attaching a nucleotide to the end or ends of a DNA sequence can be achieved either chemically or enzymetically. Methods to add a nucleotide to the ends of a DNA sequence can be found in Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

A sequence of RNA could be a good candidate for a blocking molecule. It is known that an RNA-DNA hybrid has a higher melting temperature than a DNA-DNA hybrid. In addition, RNA is a poor primer for some commonly used DNA polymerases, such as Taq polymerase used in PCR. Therefore, an unmodified RNA sequence can be used as a blocking molecule, especially in a PCR process. However, better blocking function might be achieved by modifying the RNA sequence to make it unextendable. Such modification could be, for example, adding a 3'-deoxyribonucleotide to the 3' end of the RNA sequence, a 5'-deoxyribonucleotide to the 5' end of the RNA sequence, or a 3'-deoxyribonucleotide to the 3' end and a 5'-deoxyribonucleotide to the 5' end of the RNA sequence. Methods to modify RNA sequences can be found in, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

RNA sequences can be obtained in many ways. For example, those skilled in the art may obtain a corresponding DNA sequence comprising an RNA polymerase promoter region. Then the DNA sequence is amplified, for example, by PCR. Finally, the RNA sequence then can be synthesized from the DNA sequence with an appropriate RNA polymerase and reagents. The RNA polymerase could be either T3, T7 or SP6 RNA polymerase. The DNA sequence could be obtained commercially, or by the methods mentioned above. If the DNA sequence does not contain a promoter region, it is desirable to ligate a promoter region to the DNA sequence. One skilled in the art may also clone the DNA sequence into a cloning vector comprising a promoter or promoters and produce a large quantity of the vector that is later used as a template to produce RNA transcripts. Detailed methods for synthesizing RNA can be found in Sambrook, Fritsche and Maniatis. "Molecular Cloning A laboratory Manual" $2^{nd}$ Ed. Cold Spring Harbor Press (1989), Kwoh et al., Proc. Natl. Acad. Sci. USA 86, 1173 (1989), Guatelli et al., Proc. Nat. Acad. Sci. USA, 87, 1874 (1990), which are hereby incorporated by reference in its entirety for all purposes above.

The blocking molecules can be used in combination to block multiple unwanted sequences. For example, several blocking molecules are designed to target some most abundant repetitive sequences, and these blocking molecules are used in one amplification reaction to block those targeted repetitive sequences. Preferably, 5%, 10%, 15% or 20% of the unwanted, different sequences are blocked. More preferably, 25%, 30%, 35%, 40%, 45% or 50% of the unwanted, different sequences are blocked. Most preferably, 60%, 65%, 70%, 75%, 80%, 85%, 90%, 95% or 100% of the unwanted, different sequences are blocked.

The sequence of the blocking molecule can be determined based on what sequence is desired to block. For example, if repetitive sequences are to be blocked, the blocking molecule can be designed to have complimentary sequences to the repetitive sequences. Such sequences can be commercially ordered, chemically synthesized or can be made with PCR, or cloning or other nucleic acid synthesis methods. After necessary modification as mentioned above, the sequences can be used as molecule to block repetitive sequences. Similarly, a blocking molecule can be designed to have complimentary sequences of any known sequences to block the amplification of those sequences. In addition, a specific sample of nucleic acids with unknown sequences can be isolated and be used as blocking molecules after proper modifications, if the amplification, duplication or reverse transcription of the sequences is undesirable.

Suitable nucleic acid blocking molecules may have 3, 5, 10, 15, 20, 30, 35, 40, 50, or 75 bases to 500, 700, 800, 1,000, 5,000 or 10,000 bases or more. The preferred length of the nucleic acid blocking molecule or its analogue is about 14 to 300 bases. Most preferably, the molecule has about 20 to 100 bases. Those skilled in the art will appreciate that the longer the molecule, the more specific the blocking effect of the molecule. Therefore, short blocking molecules may block a number of sequences, and the blocking effect tends to be random. Consequently, the length of the blocking molecule should be designed to achieve specific goals of applications.

The effective incubation time to achieve blocking effect depends on the length of the blocking molecule. Normally, several seconds to several minutes of incubation time is sufficient. Blocking can occur from 0° C. to 90° C. The suitable temperature for blocking depends on both the length of the blocking molecule and the nature of the molecule. For example, short blocking molecules can be used in low temperature, and it might be not effective at high temperature conditions. On the other hand, blocking molecule made of a PNA can work well at high temperature. The blocking can occur in different buffers with pH 5–10. Such buffers can be TrisHCl, Tricine, TES, HEPES, MOPS, Phosphate, acetate, citrate or any other common buffers used in chemical reactions. More information of buffers can be found in Maniatis et al., "Molecular Cloning: A Laboratory Manual," $2^{nd}$ Ed. Cold Spring Harbor Laboratory Press, Cold Spring Harbor, N.Y. (1989).

The preferred concentration to effect blocking function is 1 pM to 1 mM, more preferably, 1 nM to 100 uM, or most preferably, 10 nM to 10 uM. The blocking molecule can be dissolved in water, or any buffer mentioned above, prior to use. Effective blocking can be achieved with the presence of cations such as Na+, K+, Li+, NH4+, Mg++, Mn++, or other cations present in amplification, duplication or reverse transcription reaction buffers, and anions such as Cl−, SO4-2, CO3-2, NO3− or other anions present in amplification, duplication or reverse transcription reaction buffers, from 1 mM to 1M.

In the preferred embodiment of the invention, the blocking effect is achieved under the conditions, such as temperature, acidity, ionic strength and other parameters, similar to those of specific amplification, duplication or reverse transcription reactions. Preferably, the blocking molecule can be dissolved in most commonly used buffers to dissolve nucleic acids. Such buffers can be found in commonly used laboratory hand books, for example, in Maniatis et al., "Molecular Cloning: A Laboratory Manual," $2^{nd}$ Ed. Cold Spring Harbor Laboratory Press, Cold Spring Harbor, N.Y. (1989).

The present invention can be applied to block unwanted nucleic acid sequences in any amplification process that requires an existing nucleic acids sequence as template. Normally, PCR is the preferred amplification process used with the present invention. Further, the present invention can be used in combination with either random priming or specific priming. The random primer used in random priming PCR may have six, seven, eight, nine, ten, eleven, or more members. The random primer may comprise some partially specific sequences to target interested sequences, or they may be semi-random primers. The specific primers could be designed from known sequences or from the adapters added. The primers, either random or specific, may be attached with additional adapters for specific purposes. For example, the adapter may comprise a promoter region, a restriction site, a second primer site, or a probe. See provisional application No. 60/172,340 which is hereby incorporated by reference in its entirety for all purposes.

For convenience, in one embodiment of the present invention, the necessary reagents to carry out the present invention are packed in a research kit. The kit comprises at least the blocking molecule. Preferably, the kit comprises a solution containing the blocking molecule, a solution of an adapter comprising a primer sequence, a solution of a ligase, and a solution of corresponding primers. More preferably, the kit can further comprise a solution of restriction enzymes containing at least one restriction enzyme to fragment the nucleic acid samples.

D. Examples

Reference will now be made in detail to illustrative embodiments of the invention. While the invention will be described in conjunction with the illustrative embodiments, it will be understood that the invention is not so limited. On the contrary, the invention is intended to cover alternatives, modifications and equivalents, which may be included within the spirit and scope of the invention.

For example, DNA molecules of Human Cot-1 fraction (BRL) are blunt-ended and ligated to a T7 promoter, 100 ug RNA transcripts are made from 0.1 ug of ligated Cot-1 DNA. DNA fragments of one kb are isolated from agarose gel after digesting human DNA with Pvu II restriction enzyme. Adapters containing T3 and Sp6 promoter sites are ligated to the PvuII fragments. In a PCR reaction, use 1 ng of ligated PvuII fragments as templates, use T3 and Sp6 sequences as primer, add 1 ug Cot-1 RNA as a blocker. Other reagents are also included as required for a PCR reaction. After 30 cycles of PCR reaction, the PCR products are fragmented and end-labeled by biotin. The labeled product is used for GeneChip hybridization for genotyping assay.

We claim:

1. A method for blocking amplification of unwanted nucleic acid sequences during a nucleic acid amplification process comprising steps of:
    a) providing nucleic acid samples;
    b) blocking said unwanted nucleic acid sequences by adding blocking molecules to said samples; and
    c) non-specifically amplifying unblocked nucleic acid sequences.

2. The method of claim 1, wherein said amplification process is polymerase chain reaction.

3. The method of claim 1, wherein said blocking molecules are PNA, having 3 to 10,000 bases.

4. The method of claim 1, wherein said blocking molecules are RNA, having 3 to 10,000 bases.

5. The method of claim 1, wherein said blocking molecules are DNA, having 3 to 10,000 bases, and with a 2',3'-dideoxyribonucleotide to its 3' end.

6. The method of claim 1, wherein said blocking molecule are RNA, having 3 to 10,000 bases, and with a 3'-deoxyribonucleotide to its 3' end.

7. The method of claim 1 further comprising the steps of: fragmenting said nucleic acid samples wherein the nucleic acid is DNA.

8. The method of claim 7, wherein said fragmenting step is carried out by at least one restriction enzyme.

9. The method of claim 8, wherein said amplification process is PCR.

10. The method of claim 7, wherein said blocking molecules are PNA, having 3 to 10,000 bases.

11. The method of claim 7, wherein said blocking molecules are RNA, having 3 to 10,000 bases.

12. The method of claim 7, wherein said blocking molecules are DNA, having 3 to 10,000 bases, and with a 2',3'-dideoxyribonucleotide to its 3' end.

13. The method of claim 7, wherein said blocking molecules are RNA, having 3 to 10,000 bases, and with a 3'-deoxyribonucleotide to its 3' end.

14. A method for blocking amplification of unwanted DNA sequences during a DNA amplification process comprising steps of:
    a) providing DNA samples for amplification;
    b) fragmenting said DNA samples;
    c) attaching adapters to said fragmented DNA samples, said adapters comprising a primer region;
    d) blocking said unwanted DNA sequences by adding blocking molecules to said fragmented DNA samples, said blocking sequences being specific for unwanted DNA sequences;
    e) adding primers having complimentary sequences to said primer region in said adapters; and
    f) non-specifically amplifying unblocked, fragmented DNA samples by an amplification process.

15. The method of claim 14, wherein said fragmenting step is accomplished by restriction digestion enzymes.

16. The method of claim 14, wherein said fragmenting step is accomplished by restriction digestion enzymes and said amplifying step is accomplished by polymerase chain reaction.

17. The method of claim 16, wherein said fragmenting step is accomplished by at least two restriction digestion enzymes.

18. The method of claim 14, wherein said digesting step is accomplished by at least three restriction digestion enzymes.

19. The method of claim 14, wherein said adapters further comprise an RNA polymerase promoter sequence.

20. The method of claim 14, wherein said blocking molecules are PNA, having 3 to 10,000 bases.

21. The method of claim 14, wherein said blocking molecules are RNA, having 3 to 10,000 bases.

22. The method of claim 14, wherein said blocking molecules are DNA, having 3 to 10,000 bases, and with a 2',3'-dideoxyribonucleotide to its 3' end.

23. The method of claim 14, wherein said blocking molecules are RNA, having 3 to 10,000 bases, and with a 3'-deoxyribonucleotide to its 3' end.

24. The method of claim 7 wherein fragmenting said DNA sample is by restriction enzymes; blocking unwanted DNA sequences is by peptide nucleic acids complimentary to the unwanted DNA sequence; and amplifying unblocked, fragmented DNA samples is by polymerase chain reaction.

25. A kit for blocking unwanted nucleic acid sequences to be amplified in a non-specific amplification process comprising:
    a) a blocker comprising at least one blocking molecule, selected from the group consisting of PNA, RNA, DNA with a 2',3'-dideoxyribonucleotide at its 3' end, and RNA with a 3'-deoxyribonucleotide at its 3' end, each having 3 to 10,000 bases; and
    b) at least a pair of primers for non-specific amplification of a population of nucleic acids.

26. The kit of claim 25 further comprising: an adapter; a restriction enzyme; and a ligase.

27. The method of claim 1 wherein the nucleic acid is RNA and further comprising: synthesizing cDNA sequences from said RNA samples by reverse transcription.

28. The method of claim 27, wherein the blocking molecules are selected from the group consisting of PNA, RNA, DNA with a 2',3'-dideoxyribonucleotide to its 3' end, and RNA with a 3'-deoxyribonucleotide to its 3' end, each having 3 to 10,000 bases.

* * * * *